United States Patent
Kim et al.

(10) Patent No.: US 9,587,280 B2
(45) Date of Patent: Mar. 7, 2017

(54) METHOD FOR DETECTING A C-MET GENE USING CLEAVABLE PROBE

(71) Applicant: Samsung Life Public Welfare Foundation, Seoul (KR)

(72) Inventors: Kwang Woo Kim, Gyeongsangnam-do (KR); Jong Won Kim, Seoul (KR); Do Hyun Nam, Seoul (KR); Chang-Seok Ki, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 204 days.

(21) Appl. No.: 14/371,230

(22) PCT Filed: Jan. 9, 2013

(86) PCT No.: PCT/KR2013/000139
§ 371 (c)(1),
(2) Date: Jul. 9, 2014

(87) PCT Pub. No.: WO2013/105774
PCT Pub. Date: Jul. 18, 2013

(65) Prior Publication Data
US 2015/0247200 A1  Sep. 3, 2015

(30) Foreign Application Priority Data
Jan. 9, 2012 (KR) .......... 10-2012-0002465

(51) Int. Cl.
*C12Q 1/68* (2006.01)

(52) U.S. Cl.
CPC ......... *C12Q 1/6886* (2013.01); *C12Q 1/6851* (2013.01); *C12Q 2600/158* (2013.01)

(58) Field of Classification Search
None
See application file for complete search history.

(56) References Cited

U.S. PATENT DOCUMENTS

2011/0223598 A1* 9/2011 Opdyke ............... C12Q 1/689
435/6.11

FOREIGN PATENT DOCUMENTS

KR  10-2005-0050390 A  5/2005
KR  10-2008-0004514 A  1/2008

OTHER PUBLICATIONS

Harvey, John J. et al.: "Characterization and applications of CataCleave probe in real-time detection assays", *Analytical Biochemistry*, 333 (2004), pp. 246-255.
Takeuchi, Hiroya, et al.: "c-MET Expression Level in Primary Colon Cancer: A Predictor of Tumor Invasion and Lymph Node Metastases", *Clinical Cancer Research*, vol. 9, Apr. 2003, pp. 1480-1488.
Genbank Accession No. NM_001127500.1, Homo sapiens met proto-oncogene (hepatocyte growth factor receptor) (MET), transcript variant 1, mRNA, Dec. 18, 2011.

* cited by examiner

*Primary Examiner* — Angela M Bertagna
(74) *Attorney, Agent, or Firm* — McCarter & English, LLP

(57) ABSTRACT

One embodiment of the present invention provides a detection kit for detecting c-Met gene expression, wherein the detection kit includes a primer set which is specifically bound to the c-Met gene; and a cleavable probe which is specifically bound to the inside of a c-Met gene amplification product which is amplified by the primer set. Another embodiment of the present invention provides a method of measuring the c-Met gene expression by using the detection kit according to one embodiment of the present invention. The method according to one embodiment of the present invention is used to efficiently detect a low concentration of c-Met gene expression for cancer diagnosis and prognosis diagnosis.

15 Claims, 3 Drawing Sheets

SEQUENCE LISTING

```
<160> NUMBER OF SEQ ID NOS: 11

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      specific forward primer for amplifing c-Met

<400> SEQUENCE: 1
tcatgggtca attcagcgaa gtcctct                                           27

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      specific reverse primer for amplifing c-Met

<400> SEQUENCE: 2
tggagacact ggatgggagt cca                                               23

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      specific forward primer for amplifing c-Met

<400> SEQUENCE: 3
```
ctcctgggaa tctgcctgcg a                                       21

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      specific reverse primer for amplifing c-Met

<400> SEQUENCE: 4
tgcagccaag tctctgtgga caaac                                   25

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      specific forward primer for amplifing c-Met

<400> SEQUENCE: 5
ggcagtgcag catgtagtga ttgg                                    24

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      specific reverse primer for amplifing c-Met

<400> SEQUENCE: 6
tgatgattcc ctcggtcaga aattggg                                 27

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      catacleave probe for detecing c-Met
<220> FEATURE:
<223> OTHER INFORMATION: Description of Combined DNA/RNA Molecule:
      Synthetic catacleave probe for detecing c-Met

<400> SEQUENCE: 7
tgggacatca gagggtcgct tca                                     23

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      catacleave probe for detecing c-Met
<220> FEATURE:
<223> OTHER INFORMATION: Description of Combined DNA/RNA Molecule:
      Synthetic catacleave probe for detecing c-Met

<400> SEQUENCE: 8
aagggtctcc gctggtggtc                                         20

<210> SEQ ID NO 9
<211> LENGTH: 26
<212> TYPE: DNA
<213> ORGANISM: Artificial Sequence
<220> FEATURE:

```
<223> OTHER INFORMATION: Description of Artificial Sequence: Synthetic
      catacleave probe for detecing c-Met
<220> FEATURE:
<223> OTHER INFORMATION: Description of Combined DNA/RNA Molecule:
      Synthetic catacleave probe for detecing c-Met

<400> SEQUENCE: 9
gcccagtagc cugaugugc atttca                                          26

<210> SEQ ID NO 10
<211> LENGTH: 520
<212> TYPE: DNA
<213> ORGANISM: Artificial Sequence
<220> FEATURE:
<223> OTHER INFORMATION: Description of Artificial Sequence: Synthetic
      MET-1 sequence

<400> SEQUENCE: 10
agagtttacc acagctttgc agcgcgttga cttattcatg ggtcaattca gcgaagtcct    60
cttaacatct atatccacct tcattaaagg agacctcacc atagctaatc ttgggacatc   120
agagggtcgc ttcatgcagg ttgtggtttc tcgatcagga ccatcaaccc ctcatgtgaa   180 tttctcctg gactcccatc cagtgtctcc agaagtgatt gtggagcata cattaaacca   240
aaatggctac acactggtta tcactgggaa gaagatcacg aagatcccat gaatggctt    300 gggctgcaga catttccagt cctgcagtca atgcctctct gccccaccct ttgttcagtg   360
tggctggtgc cacgacaaat gtgtgcgatc ggaggaatgc ctgagcggga catggactca   420
acagatctgt ctgcctgcaa tctacaaggt tttcccaaat agtgcacccc ttgaaggagg   480
gacaaggctg accatatgtg gctgggactt tggatttcgg                          520

<210> SEQ ID NO 11
<211> LENGTH: 461
<212> TYPE: DNA
<213> ORGANISM: Artificial Sequence
<220> FEATURE:
<223> OTHER INFORMATION: Description of Artificial Sequence: Synthetic
      MET-2 sequence

<400> SEQUENCE: 11
ctcagtgctc taaatccaga gctggtccag gcagtgcagc atgtagtgat tgggcccagt    60
agcctgattg tgcatttcaa tgaagtcata ggaagagggc attttggttg tgtatatcat   120
gggactttgt tggacaatga tggcaagaaa attcactgtg ctgtgaaatc cttgaacaga   180
atcactgaca taggagaagt ttcccaattt ctgaccgagg gaatcatcat gaaagatttt   240
agtcatccca atgtcctctc gctcctggga atctgcctgc gaagtgaagg gtctccgctg   300
gtggtcctac catacatgaa acatggagat cttcgaaatt tcattcgaaa tgagactcat   360
aatccaactg taaaagatct tattggcttt ggtcttcaag tagccaaagg catgaaatat   420
cttgcaagca aaagtttgt ccacagagac ttggctgcaa g                        461
```

METHOD FOR DETECTING A C-MET GENE USING CLEAVABLE PROBE

This application is a 371 of PCT/KR2013/000139 filed on Jan. 9, 2013, published on Jul. 18, 2013 under publication number WO 2013/105774, which claims priority benefits from Korean Patent Application Number 10-2012-0002465 filed Jan. 9, 2012, the disclosure of which is incorporated herein by reference.

TECHNICAL FIELD

The present invention relates to a cancer diagnosis kit and a diagnosis method using the same. More specifically, the present invention relates to a kit enabling to detect a gene in real-time by using a primer set and a cleavable probe and a diagnosis method using the same.

DESCRIPTION OF THE RELATED ART c-Met is a hepatocyte growth factor (HGF) receptor, and HGF is a kind of cytokine which is bound to an extracellular region of c-Met receptor tyrosine kinase to cause division, movement, morphogenesis, and angiogenesis in various normal cells and tumor cells. c-Met is a representative receptor tyrosine kinase existing on a cell surface. Since c-Met itself is an oncogenic gene and sometimes involved in various tumor-related mechanisms such as oncogenesis, metastasis, cancer cell migration, cancer cell invasion, and angiogenesis regardless of HGF, which is the ligand, c-Met is a protein that is drawing attention as a anticancer target.

In addition, c-Met is overexpressed in many types of cancer. In particular, it is known that c-Met overexpression is mostly involved in the causes of bad prognosis in patients. Therefore, a primer set which may specifically amplify a c-Met gene may be used to measure cancer progress in a patient by using a clinical sample taken from a patient. In addition, the primer set may be used as important decision-making information to select a cancer therapeutic agent or a therapeutic method. Therefore, it is required to develop a primer or probe which is specifically bound to a gene or an mRNA of c-Met or a diagnosis kit which enables to verify the degree of overexpression of the c-Met gene or mRNA.

Recently, polymerase chain reaction (PCR) is used for detection or amplification of a gene. Realization of high-throughput PCR screening using PCR has caused innovative changes in modern biology and medicine. The analytical technology had a great effect on some research areas including diagnosis, environmental monitoring, blood test, and genotyping. With the arrival of bioinformatics, scientist has become able to process genetic information more than any time before. Nevertheless, many studies are conducted to be able to detect a smaller amount of DNA and verify the amplified amount in real-time.

Therefore, the PCR method was improved to develop a method of detecting the c-Met gene which may be used more effectively in cancer diagnosis. On the basis of the results, the probe-based detection kit and the diagnosis method of the present invention were developed.

DETAILED DESCRIPTION OF THE INVENTION

Technical Problem

An embodiment of the present invention provides a c-Met gene detection kit including a primer set and a cleavable probe.

Another embodiment of the present invention provides a method of detecting c-Met gene by using the c-Met gene detection kit including a primer set and a cleavable probe.

Technical Solution

According to an aspect of the present invention, there is provided a detection kit for detecting c-Met gene expression, wherein the detection kit includes a primer set which is specifically bound to the c-Met gene; and a cleavable probe which is specifically bound to the inside of a c-Met amplification product which is amplified by the primer set.

An embodiment of the present invention provides a c-Met gene detection kit including a primer including a nucleic acid of SEQ ID NO: 1 a primer including a nucleic acid of SEQ ID NO: 2, and a cleavable probe including a nucleic acid of SEQ ID NO: 7.

Another embodiment of the present invention provides a c-Met gene detection kit including a primer including a nucleic acid of SEQ ID NO: 3, a primer including a nucleic acid of SEQ ID NO: 4, and a cleavable probe including a nucleic acid of SEQ ID NO: 8.

Another embodiment of the present invention provides a c-Met gene detection kit including a primer including a nucleic acid of SEQ ID NO: 5, a primer including a nucleic acid of SEQ ID NO: 6, and a cleavable probe including a nucleic acid of SEQ ID NO: 9.

The term "c-Met gene" used herein refers to a gene encoding receptor tyrosine kinase which is bound to hepatocyte growth factor (HGF). For example, a c-Met gene may be corresponding to GenBank Accession Number NM_000245 or GenBank Accession Number NM_000236.

c-Met protein is overexpressed in many types of cancer. In particular, it is known that c-Met overexpression is mostly involved in the causes of bad prognosis in patients. The types of cancer which may be diagnosed by measuring the overexpression of the c-Met gene which may cause overexpression of c-Met protein may include carcinoma, lymphoma, blastoma, sarcoma, and leukemia, but are not limited thereto. The cancer includes, for example, bladder cancer, breast cancer, cervical cancer, cholangiocarcinoma, colorectal cancer, endometrial cancer, esophageal cancer, gastric cancer, head and neck cancer, kidney cancer, liver cancer, lung cancer, nasopharyngeal carcinoma, ovarian cancer, pancreatic cancer, gallbladder cancer, prostate cancer, thyroid cancer, osteosarcoma, rhabdomyosarcoma, synovial sarcoma, Kaposi's sarcoma, leiomyosarcoma, malignant fibrous histiocytoma, fibrosarcoma, adult T-cell leukemia, lymphoma, multiple myeloma, neuroblastoma/astrocytoma, melanoma, mesothelioma, and Wilms tumor, but is not limited thereto.

The term "primer" used herein may be used interchangeably with "oligonucleotide" or "polynucleotide." The primer refers to an oligonucleotide which serves as a starting point to being DNA synthesis in PCR. A primer generally includes from about 15 to about 35 nucleotides and is hybridized with complementary regions of the target sequence.

The term "probe" used herein refers to an oligonucleotide which is specifically bound to a target sequence, and includes, for example, a polynucleotide including a specific region which is designed to be hybridized by a sequence-specific method with a complementary region of a specific nucleic acid sequence such as a target nucleic acid sequence. In one embodiment of the present invention, the oligonucleotide probe includes from about 15 to about 60 nucleotides. Appropriately, the oligonucleotide probe includes from about 18 to about 30 nucleotides.

The term "cleavable probe" used herein refers to a probe including two types of nucleic acid, for example, a DNA probe including some RNA nucleotides inside the DNA probe. The cleavable probe may include an internal region in which from about one to about ten DNA nucleotides are substituted with RNA nucleotides, in which from about two to about eight DNA nucleotides are substituted with RNA nucleotides, or in which from about three to about seven DNA nucleotides are substituted with RNA nucleotides, but is not limited thereto. In addition, RNA nucleotides may be positioned inside a probe consecutively or non-consecutively. Appropriately, the cleavable probe may be one of the probes of SEQ ID NOS: 7 to 9, but is not limited thereto.

In addition, the cleavable probe may be labeled with a detectable material at both ends or inside of the probe. A mixture for PCR includes an RNase enzyme which may specifically cleave an RNA sequence part of an RNA-DNA double strand. After the cleavage by an RNase, all the fragments of a cleavable probe are dissociated from a target amplicon at a reaction temperature and dispersed in a reaction solution. As donors and acceptors labeled in the probe are separated, fluorescence emission by the donors may be monitored.

The term "label" or "detectable label" used herein refers to a fluorochrome compound which is bound to a probe by a covalent bond or a noncovalent bond, and may be a fluorescence resonance energy transfer (FRET) pair including a fluorescent donor and a fluorescent acceptor.

The term "fluorochrome" used herein refers to a fluorescent compound which emits light by being excited by light having a wavelength shorter than that of the emitted light. In addition, the term "fluorescent donor" refers to a fluorochrome which emits light measured by the assay disclosed in the present invention. In addition, a fluorescent donor may provide light which is absorbed by a fluorescent acceptor. The term "fluorescent acceptor" used herein refers to a secondary fluorochrome or a quencher which absorbs energy emitted from a fluorescent donor. A secondary fluorochrome absorbs energy emitted from a fluorescent donor and then emits light having a wavelength longer than that of the light emitted by a fluorescent donor. A quencher absorbs energy emitted from a fluorescent donor.

Any light-emitting molecules, appropriately, a fluorochrome and/or a quencher, may be used in an embodiment of the present invention. For example, the light-emitting molecule may be Alexa Fluor 350, Alexa Fluor 430, Alexa Fluor 488, Alexa Fluor 532, Alexa Fluor 546, Alexa Fluor 568, Alexa Fluor 594, Alexa Fluor 633, Alexa Fluor 647, Alexa Fluor 660, Alexa Fluor 680, 7-diethylaminocoumarin-3-carboxylic acid, fluorescein, Oregon Green 488, Oregon Green 514, tetramethyl rhodamine, rhodamine X, Texas Red dye, QSY 7, QSY33, Dabcyl, BODIPY FL, BODIPY 630/650, BODIPY6501665, BODIPY TMR-X, BODIPY TR-X, dialkylaminocoumarin, Cy3 (cyanine 3), Cy3.5, Cy5.5, Cy5, DTPA ($Eu^{3+}$)-AMCA, and TTHA ($Eu^{3+}$) AMCA, but is not limited thereto. Appropriately, a light-emitting molecule may be a FRET including of 6-FAM and Iowa Black BQ, but is not limited thereto.

In addition, the kit for detecting c-Met gene may further include a thermostable polymerase or RNase, and enzymes included in the kit may be a thermostable polymerase and a thermostable RNase.

The term "thermostable" herein used and applied to an enzyme refers to an enzyme maintaining biological activity at an increased temperature (e.g., 55° C. or higher), or in a cycle in which heating and cooling are repeated. A thermostable polynucleotide polymerase may be used especially in a PCR amplification reaction. In an embodiment of the present invention, the thermostable polynucleotide polymerase may be Taq polymerase. The thermostable polynucleotide polymerase may be a Taq polymerase selected from the group consisting of AmpliTaq, AmpliTaq Stoffel fragment, SuperTaq, SuperTaq plus, LA Taq, LApro Taq, and EX Taq. In addition, the term "RNase" used herein refers to an enzyme specifically cleaving an RNA. The RNA may be a double-stranded RNA which may be a hybridized double-strand formed by hybridization of an RNA and a DNA.

In addition, the kit may be provided as a kit including a package unit having one or more reagents. The kit may include at least one selected from the group consisting of the following articles: a buffer, instruction, and a positive or negative control group. The kit may include containers of reagents which are mixed at an appropriate ratio to perform the method described herein. The regent containers appropriately include a unit number of reagent to omit measuring when the method is performed. In another embodiment of the present invention, the kit reagent further includes a reagent for extracting genome DNA or RNA from a biological sample. In addition, the kit reagent may include a reagent to be applied to a reverse transcriptase-PCR analysis.

Another aspect of the present invention provides a method of detecting c-Met gene, the method including:

obtaining DNA from a sample;

mixing with a sample at least one primer-probe set selected from the group consisting of a first primer-probe set including a primer including a nucleic acid of SEQ ID NO: 1, a second primer including a nucleic acid of SEQ ID NO: 2 and a cleavable probe including a nucleic acid of SEQ ID NO: 7; a second primer-probe set including a primer including a nucleic acid of SEQ ID NO: 3, a primer including a nucleic acid of SEQ ID NO: 4 and a cleavable probe including a nucleic acid of SEQ ID NO: 8; and a third primer-probe set including a primer including a nucleic acid of SEQ ID NO: 5, a primer including a nucleic acid of SEQ ID NO: 6 and a cleavable probe including a nucleic acid of SEQ ID NO: 9 to prepare a mixture;

mixing a polymerase, an RNase, and an amplification buffer to the mixture to amplify DNA in the mixture; and detecting an increase of a signal emitted from the label on the probe.

The method of detecting c-Met gene is described in details below.

First, the method of detecting c-Met gene may include obtaining DNA from a sample. A sample may be obtained from a cancer patient or a person who wants to undergo diagnosis of cancer progress, or a specific body part.

The DNA may be a gDNA (genomic DNA), a cDNA (complementary DNA) or a DNA fragment. The DNA may be obtained directly from a cell. In addition, to detect DNA expression, an mRNA may be obtained from a cell and then a cDNA may be obtained from the mRNA by performing a reverse transcriptase PCR.

Subsequently, the method of detecting c-Met gene may include mixing with a sample at least one primer-probe set selected from the group consisting of a first primer-probe set including a primer including a nucleic acid of SEQ ID NO: 1, a second primer including a nucleic acid of SEQ ID NO: 2 and a cleavable probe including a nucleic acid of SEQ ID NO: 7; a second primer-probe set including a primer including a nucleic acid of SEQ ID NO: 3, a primer including a nucleic acid of SEQ ID NO: 4 and a cleavable probe including a nucleic acid of SEQ ID NO: 8; and a third primer-probe set including a primer including a nucleic acid of SEQ ID NO: 5, a primer including a nucleic acid of SEQ ID NO: 6 and a cleavable probe including a nucleic acid of SEQ ID NO: 9 to prepare a mixed sample.

The cleavable probe may be labeled with a detectable material at both ends or inside of the probe and may be labeled with a fluorescence resonance energy transfer (FRET) pair including a fluorescent donor and a fluorescent acceptor.

Subsequently, the method of detecting c-Met gene may include mixing a polymerase, an RNase, and an amplification buffer to the mixed sample to amplify DNA in the mixture. Any thermostable polymerase or RNase may be used.

The term "amplification buffer" refers to a compound which is added to an amplification reaction to control the amplification reaction and thereby modify the stability, activity, and/or lifecycle of at least one element of the amplification reaction. The buffer may be compatible with PCR amplification and RNase H cleavage activity. Examples of the buffer include a buffer including 4-(2-hydroxyethyl)-1-piperazine ethane sulfonic acid (HEPES), 3-(N-morpholino) propane sulfonic acid (MOPS), acetate or phosphate, but are not limited thereto.

A PCR buffer may generally include about 70 mM or lower KCl, about 1.5 mM or higher $MgCl_2$, and from about 50 to about 200 µM of each dATP, dCTP, dGTP and dTTP. The buffer may further include an additive for an efficient reverse transcriptase PCR or to optimize a PCR.

An additive is a compound which is added to modify the stability, activity, and/or lifecycle of at least one element of the composition. Examples of the additive include betaine, formamide, KCl, $CaCl_2$, MgOAc, $MgCl_2$, NaCl, $NH_4OAc$, NaI, $Na(CO_3)_2$, LiCl, MnOAc, NMP, trehalose, Demiethyl sulfoxide (DMSO), glycerol, ethylene glycol, dithiothreitol (DTT), pyrophosphatase, inorganic pyrophosphatase (TAP), a cation, and other compounds, proteins, or cofactors which may modify the amplification efficiency, but are not limited thereto. The additive may be selectively added to improve selectivity for primer annealing.

Subsequently, the method of detecting c-Met gene may include detecting an increase of a signal emitted from the label on the probe. The emitted signal may be fluorescence. The result of fluorescence emission may be detected by using an appropriate device such as Applied Biosystems 7500 Fast Real-Time PCR System or Biorad CFX96 real-time PCR thermocycler, but all devices available in the art may be used.

Additionally, the method of detecting c-Met gene may include a reverse transcription PCR in which an RNA is obtained from a sample and amplified the RNA by using a reverse transcriptase to provide the resulting cDNA as a sample DNA. An RNA may be taken from a cancer patient or a person who wants to undergo cancer diagnosis, and then the RNA may be amplified by using a reverse transcriptase to obtain a cDNA. Reverse transcription to a cDNA by using a reverse transcriptase may be performed by any methods available in the art.

In the reverse transcription PCR, a template-specific DNA primer is used to produce a complementary DNA strand. Then, in a PCR, the product is modified, and a second template-specific primer is bound to the cDNA and is extended to form a duplex DNA. The resulting product is amplified in the next temperature cycle. To maintain the highest sensitivity, it is important to prevent the RNA from being degraded before cDNA synthesis.

The method of detecting the c-Met gene may be used to verify expression of the c-Met and thereby diagnose carcinoma, lymphoma, blastoma, sarcoma, and leukemia, but are not limited thereto. Specifically, the cancer includes bladder cancer, breast cancer, cervical cancer, cholangiocarcinoma, colorectal cancer, endometrial cancer, esophageal cancer, gastric cancer, head and neck cancer, kidney cancer, liver cancer, lung cancer, nasopharyngeal carcinoma, ovarian cancer, pancreatic cancer, gallbladder cancer, prostate cancer, thyroid cancer, osteosarcoma, rhabdomyosarcoma, synovial sarcoma, Kaposi's sarcoma, lelomyosarcoma, malignant fibrous histiocytoma, fibrosarcoma, adult T-cell leukemia, lymphoma, multiple myeloma, neuroblastoma/astrocytoma, melanoma, mesothelioma, and Wilms tumor, but is not limited thereto.

Advantageous Effects

When the primer set and the cleavable probe according to one embodiment of the present invention, wherein the primer set and the cleavable probe are specifically bound to c-Met, are used, a very little amount of c-Met expression may be detected in real-time, and thus various cancers related with c-Met overexpression may be diagnosed and the prognosis may be easily determined.

EXAMPLES

Hereinafter, the present invention is described in more detail with reference to the examples below. However, these examples are for illustrative purposes only and are not intended to limit the scope of the invention.

Example 1

Preparation of Primer Set and Probe for c-Met Detection

A total of three sets of a primer set and a primer for c-Met detection (F: forward primer, R: reverse primer, IN: Cata-Cleave probe) were prepared (synthesized by Integrated DNA Technologies, Inc.).

TABLE 1

| Set no. | ID | sequences | SEQ ID NO | Binding site | Length (bp) |
|---|---|---|---|---|---|
| 1 | F | TCATGGGTCAATTC AGCGAAGTCCTCT | SEQ ID NO: 1 | Exon 3 | 27 |
|  | IN | TGGGACATCagagG GTCGCTTCA | SEQ ID NO: 7 | Exon 3-4 | 23 |
|  | R | TGGAGACACTGGAT GGGAGTCCA | SEQ ID NO: 2 | Exon 4 | 23 |
| 2 | F | CTCCTGGGAATCTG CCTGCGA | SEQ ID NO: 3 | Exon 17 | 21 |

TABLE 1-continued

| Set no. | ID | sequences | SEQ ID NO | Binding site | Length (bp) |
|---|---|---|---|---|---|
|  | IN | AAGGGTCTccgcTG GTGGTC | SEQ ID NO: 8 | Exon 17 | 20 |
|  | R | TGCAGCCAAGTCTC TGTGGACAAAC | SEQ ID NO: 4 | Exon 18 | 25 |
| 3 | F | GGCAGTGCAGCATG TAGTGATTGG | SEQ ID NO: 5 | Exon 15 | 24 |
|  | IN | GCCCAGTAGCCuga uTGTGCATTTCA | SEQ ID NO: 9 | Exon 15 | 26 |
|  | R | TGATGATTCCCTCG GTCAGAAATTGGG | SEQ ID NO: 6 | Exon 17 | 27 |

In the Table 1, the nucleotide presented as a small letter is RNA.

In addition, the two DNA ends of the CataCleave probe, which is a cleavable probe, were labeled by using 6-FAM, which is a fluorochrome, at the 5'-end and Iowa Black RQ, which is a quencher, at the 3'-end.

Example 2

Sampling

MET-1 gene (SEQ ID NO: 10) was used for the positive reaction of Set No. 1 and Set No. 2, while MET-2 gene (SEQ ID NO: 11) was used for the positive reaction of Set No. 3. A polynucleotide encoding the gene sequence was inserted to the EcoR1/BamH1 site of pGEM-3Z (Promega) to prepare a positive sample.

Example 3 c-Met Gene Detection by Using Primer Set and Probe for c-Met Detection

Figure 1:
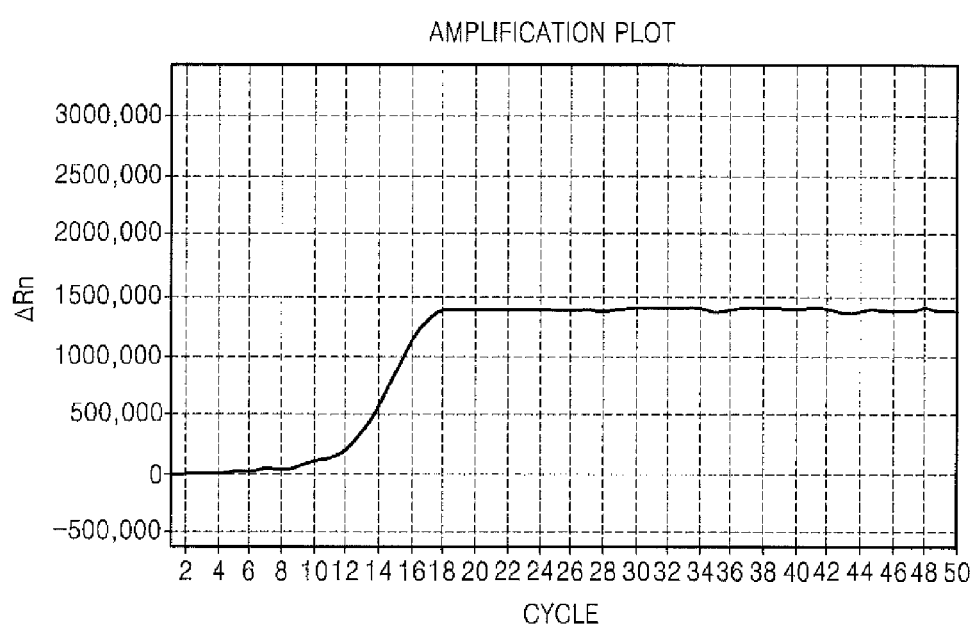
FIG. 1 shows the experimental result of amplifying a c-MET target nucleotide sequence by using the primer-probe set no. 1.
Figure 2:
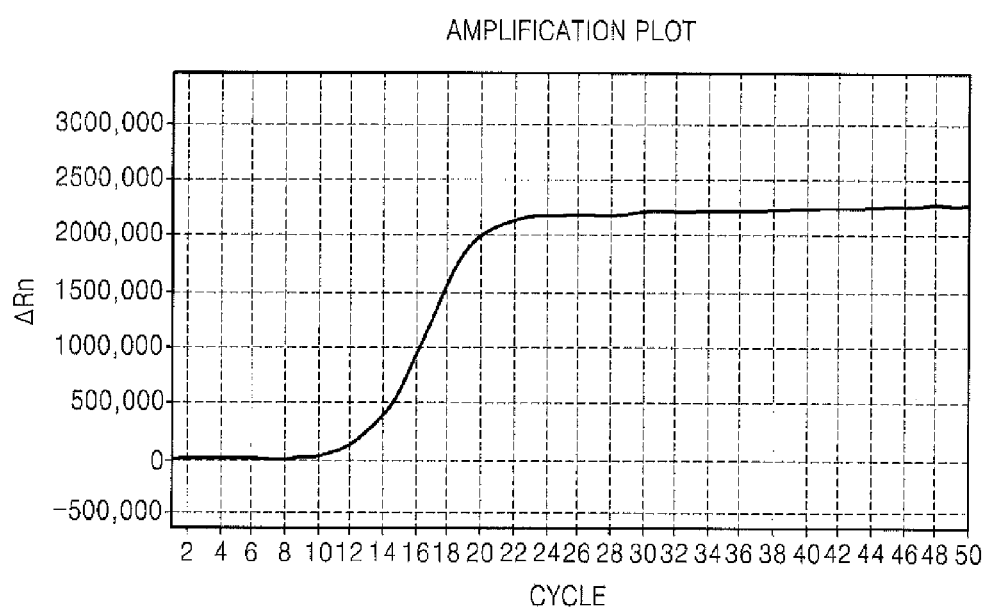
FIG. 2 shows the experimental result of amplifying a c-MET target nucleotide sequence by using the primer-probe set no. 2.
Figure 3:
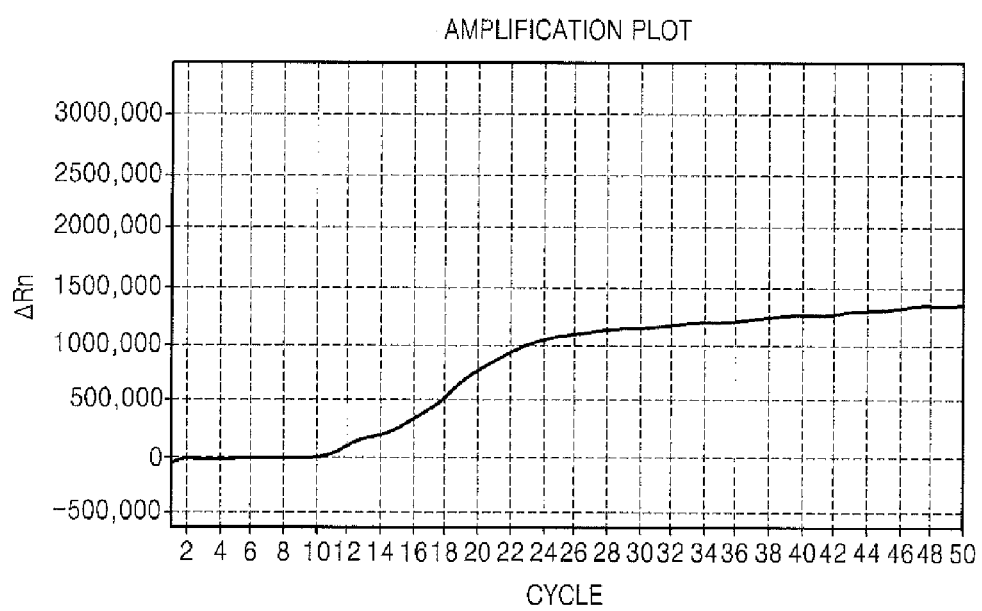
FIG. 3 shows the experimental result of amplifying a c-MET target nucleotide sequence by using the primer-probe set no. 3.

The primer, probe, amplification buffer (32 mM HEPES-KOH, pH 7.8, 100 mM potassium acetate, 4 mM magnesium acetate, 0.11% bovine serum albumin, 1% dimethyl sulfoxide), dUTP/NTP mix (80 pM of each dGTP, dCTP, dATP and 160 µM of dUTP), 2.5 units of *Thermus aquaticus* DNA polymerase, 1 unit of *Pyrococcus furiosis* HII, and 0.1 unit of uracil-N-glycosylase were used to perform a PCR in RABI7500 (Applied Biosystem) according to the following cycling protocol: initial denaturation at 95° C. for 5 minutes; 50 cycles of denaturation at 95° C. for 10 seconds, annealing at 65° C. for 10 seconds, and amplification at 72° C. for 40 seconds; final extension at 72° C. for 5 min. FAM emission was monitored when the temperature was 65° C. (Refer to FIGS. 1 to 3).

INDUSTRIAL APPLICABILITY

When the primer and the probe according to one embodiment of the present invention are used, c-Met gene at a very low concentration in comparison with the concentration for a general PCR may be easily detected. Therefore, the primer-probe set according to one embodiment of the present invention may be used to determine expression of c-Met gene after performing a reverse transcription PCR.

What is claimed is:

1. A c-Met gene detection kit comprising SEQ ID NO: 5, SEQ ID NO: 6, and SEQ ID NO: 9, wherein SEQ ID NOs: 5 and 6 are nucleic acid primers and SEQ ID NO: 9 is a cleavable nucleic acid probe.

2. The c-Met gene detection kit of claim 1, further comprising a nucleic acid primer of SEQ ID NO: 1, a nucleic acid primer of SEQ ID NO: 2, and a cleavable nucleic acid probe of SEQ ID NO: 7.

3. The c-Met gene detection kit of claim 2, wherein the e-Met gene detection kit further comprises a thermostable polymerase and a RNase.

4. The c-Met gene detection kit of claim 2, wherein at least one cleavable nucleic acid probe is labeled with a detectable material at both ends of the probe or inside the probe.

5. The c-Met gene detection kit of claim 4, wherein the detectable material is a fluorescence resonance energy transfer (FRET) pair.

6. The c-Met gene detection kit of claim 1, further comprising a nucleic acid primer of SEQ ID NO: 3, a nucleic acid primer of SEQ ID NO: 4, and a cleavable nucleic acid probe of SEQ ID NO: 8.

7. The c-Met gene detection kit of claim 6, wherein the c-Met gene detection kit further comprises a thermostable polymerase and a RNase.

8. The c-Met gene detection kit of claim 3, wherein at least one cleavable nucleic acid probe is labeled with a detectable material at both ends of the probe or inside the probe.

9. The c-Met gene detection kit of claim 8, wherein the detectable material is a fluorescence resonance energy transfer (FRET) pair.

10. The c-Met gene detection kit of claim 1, wherein the c-Met gene detection kit further comprises a thermostable polymerase and a RNase.

11. The c-Met gene detection kit of claim 1, wherein the cleavable nucleic acid probe is labeled with a detectable material at both ends of the probe or inside the probe.

12. The c-Met gene detection kit of claim 11, wherein the detectable material is a fluorescence resonance energy transfer (FRET) pair.

13. A method of detecting a c-Met gene, the method comprising:
    obtaining DNA from a sample;
    mixing the DNA with a primer-probe set comprising SEQ ID NO: 5, SEQ ID NO: 6, and SEQ ID NO: 9 to prepare a mixture, wherein SEQ ID NOs: 5 and 6 are nucleic acid primers and SEQ ID NO: 9 is a cleavable nucleic acid probe;
    mixing a polymerase, an RNase, and an amplification buffer with the mixture and amplifying DNA in the mixture; and
    detecting an increase of a signal emitted from a label on the probe, thereby detecting a c-Met gene.

14. The method of claim 13, wherein the method further comprises mixing the mixture with a second primer-probe set that includes a nucleic acid primer of SEQ ID NO: 1, a nucleic acid primer of SEQ ID NO: 2, and a cleavable nucleic acid probe SEQ ID NO: 7.

15. The method of claim 14, wherein the method further comprises mixing the mixture with a third primer-probe set that includes a nucleic acid primer of SEQ ID NO: 3, a nucleic acid primer of SEQ ID NO: 4, and a cleavable nucleic acid probe of SEQ ID NO: 8.

* * * * *